US00PP12077P2

(12) United States Plant Patent
Carpenter

(10) Patent No.: US PP12,077 P2
(45) Date of Patent: Sep. 4, 2001

(54) CYMBIDIUM, ORCHID PLANT NAMED 'EVERGLADES GOLD'

(76) Inventor: Milton Carpenter, 1101 Tabit Rd., Belle Glade, FL (US) 33430

( * ) Notice: Subject to any disclaimer, the term of this patent is extended or adjusted under 35 U.S.C. 154(b) by 0 days.

(21) Appl. No.: 09/330,321

(22) Filed: Jun. 11, 1999

(51) Int. Cl.[7] ..... A01H 5/00
(52) U.S. Cl. ..... Plt./311
(58) Field of Search ..... Plt./311

(56) References Cited

U.S. PATENT DOCUMENTS

P.P. 11,395 * 5/2000 Holm ..... Plt./311

* cited by examiner

*Primary Examiner*—Bruce R. Campell
*Assistant Examiner*—Wendy C. Baker
(74) *Attorney, Agent, or Firm*—Howard A. Kenyon

(57) ABSTRACT

A distinct cultivar of Cymbidium plant named 'Everglades Gold', characterized by a compact, upright growth habit with particular vigor in summer temperatures with a diurnal range of 70–95 degrees Fahrenheit, that is not normally characteristic of Cymbidium. Leaves are of intermediate diameter, upright till of length of approximately 20" when they arch outwardly. The intensely colored cadmium yellow flowers are carried on a fleshy, erect peduncle without any arching character. Flowers will maintain quality with no obvious senescence for a minimum of 35 days in 70–95 degree Fahrenheit temperature range.

3 Drawing Sheets

BACKGROUND OF THE INVENTION

The present invention relates to a new and distinct cultivar of Cymbidium plant, botanically known as Milton Carpenter (Cymbidium Golden Elf 'Sundust'×Cymbidium Via Ambarino 'Highland'), registered with The Royal Horticultural Society in England in 1992, hereinafter referred to by the cultivar name 'Everglades Gold'.

This new cultivar is the product of a crossing using the above parents by the inventor in Belle Glade, Fla. Pollination was effected on Jun. 12, 1987. The inventor's object was to produce a Cymbidium that would grow and flower freely in the warm temperature regime of South Florida. The cultivar 'Everglades Gold' appeared in February 1995 as a single outstanding plant among a large seedling population of the grex at Everglades Orchids Inc., an orchid nursery owned by the applicant in Belle Glade, Fla.

Comparison testing by the inventor at his Belle Glade nursery has established the following differences between the Cymbidium 'Everglades Gold' and other siblings from the same parentage:

(1) Plants of 'Everglades Gold' grown faster under comparable conditions than any other seedling from the same crossing.

(2) The plant of 'Everglades Gold' was among the first seedlings from the crossing to bloom with an initial inflorescence of flowers fully open on Feb. 16th, 1995 which is seven years and eight months after pollination.

(3) Flowers of 'Everglades Gold' with a horizontal natural spread of 4⅜" and a vertical natural spread of 4⅛" are larger in both dimensions than all other seedlings from the same crossing.

(4) The intense cadmium yellow sepals and petals of 'Everglades Gold' are unlike all other seedlings in the crossing.

(5) Vegetative divisions of 'Everglades Gold' resist transplant shock and will continue on a six monthly flowering cycle over a wide range of cultural practices.

(6) Leaves of 'Everglades Gold' are intermediate in width and length between both parents and are in the range of ⅞–1.0" diameter and 24–28" length when mature.

Asexual propagation by division and meristem tissue culture has been carried out at the laboratories of b.v. Floricultura in Heemstede, Holland. Plants of 'Everglades Gold' are stable and have bloomed without any phenotypic variation being observed.

SUMMARY OF THE INVENTION

After discovery in February 1995, 'Everglades Gold' has been observed under a wide range of environmental conditions. No mutation or variance in the genotype has been observed as the result of vegetative division or tissue culture. Phenotypic variation has been limited to a slight reduction in yellow color intensity of flower segments of blooms produced between November 1st and February 15th.

The following traits have been observed at all bloomings since February 1995 and are considered unique to the cultivar 'Everglades Gold'. In combination they distinguish 'Everglades Gold' as a new and distinct cultivar:

(1) Rapid growth rate and resistance to transplant shock.

(2) Longer lasting flowers, at 35 days, uncut, than all other seedlings from the same parentage.

(3) Larger flowers,, at 4⅜ horizontal natural spread, than all other seedlings from the same parentage.

(4) The plant carries normally only four leaf pairs (8 leaves) on each newly mature pseudobulb. The blubs show slight traces of anthrocyanin pigment when plants are grown under 3–5,000 foot candles of incident light.

BRIEF DESCRIPTION OF THE PHOTOGRAPHS

Accompanying color pictures illustrate the overall appearance of the new cultivar with colors as true as is possible to obtain in color reproductions of this type. The pictures were taken in November 1999 so they represent a yellow color intensity at the lower end of typical for the cultivar.

The first picture shows three blooms of the new variety of orchid.

The second picture is a close-up view of the bloom of the new variety of orchid.

The third picture shows an entire plant of the new variety of orchid.

DETAILED BOTANICAL DESCRIPTION

In the following description color references are made to The Royal Horticultural Society Color Chart except where general color terms are used. Observations and measurements are made from plants grown in Belle Glade, Fla. in a glass topped greenhouse with screen sidewalls. Night temperatures normally range between 54–78 degrees Fahrenheit annually and day temperatures between 78–100 degrees Fahrenheit.

(A) Botanical Classification: Cymbidium (Golden Elf 'Sundust'×Via Ambarino 'Highland') cultivar 'Everglades Gold'.

(B) Parentage: Female parent — Golden Elf 'Sundust', a hybrid of *Cymbidium ensifolium* 'Album'×Cymbidium Enid Haupt 'Dos Pueblos'.

(C) Parentage: Male parent — Via Ambarino 'Highland', a hybrid of Cymbidium Via Cox×Cymbidium Thanksgiving 'Nativity'.

(D) Propagation: By vegetative division and tissue culture. Time interval from excision of apical and lateral meristem till delivery of 1,000 rooted plants in vitro, 338 days.

(E) Plant Description:

*Shape.*—Upright to outwardly arching leaves with strongly erect flower stems arising from above ground pseudobulbs of approximately 4" height. Mature plants, multispiking in 6" diameter containers.

*Height.*—Approximately 20" from the surface of the potting medium to the leaf point of arching.

*Vigor.*—Extremely vigorous with resistance to transplant shock and a six-monthly growth maturation cycle which results in increases blooming frequency.

*Time to finishing.*—Under observed cultural conditions a single growth 6–8" meristem can be expected to produce it's first inflorescence 24–30 months after deflasking (removal from in-vitro culture).

*Leaves.*—8 leaves per pseudobulb. Leaves are linear to ligulate with a semi-circular base ensheathing the pseudobulbs and acute tips with an entire margin. The leaf margin is non-dentate and slightly downward recurving. The leaf texture is moderately smooth on both surfaces with slight longitudinal ribbing in addition to the pronounced midrib. The upper and lower leaf surfaces are RHS 143 A in color.

*Pseudobulbs.*—Normally not more than six per 6" container. Shape is slightly elongate, circular, about 3½" in height. Mid green, RHS 141A with low levels of anthrocyanin although new growths carry strong pigmentation until leaf elongation commences. After leaf dehiscence, pseudobulbs have a waxy texture with four distinct lines of circumference.

Flower description:

*Arrangement.*—Large yellow flowers arranged bilaterally on the raceme. Typically the flower count will average 11–13 when the plant is 36 months from in-vitro deflasking. Flowering intermittent with a peak near the Spring and Fall equinox. Usually double inflorescences will be produced contemporaneously on each newly matured pseudobulb and the flowers are persistent. Petals and sepals ar held flat with slight forward projection of the dorsal sepal. The labellum is open with slight recurving on the proximal margin. All segments are pointed, petals are more pronounced than sepals.

*Longevity.*—Inflorescences typically last in excess of 30 days in a wide range of environmental conditions but uncut. Cut inflorescences have a greatly diminished shelf life.

*Size.*—Horizontal natural spread — 4⅜".

*Vertical natural spread.*—4⅛".

*Flower pedical.*—2½".

*Gynandrium depth.*—1½".

*Gynandrium width.*—½".

*Petals.*—3¼".

*Petals.*—Width 1½".

*Petals.*—Shape — elliptic with an acute apex.

*Petals.*—Texture — smooth.

*Petals.*—Color — color fan 1, yellow group 13(A).

*Sepals.*—Length 2½".

*Sepals.*—Width — 1⅓".

*Sepals.*—Texture — smooth.

*Sepals.*—Color — color fan 1, yellow group 13(A).

*Labellum.*—Length — 2⅛".

*Labellum.*—Width 1⅓".

*Labellum.*—Keel — color fan 1, yellow group 12(B).

*Labellum color.*—Color fan 1, yellow group 12(B) labellum stitched in red (color fan 1, red group 42A) which coalesces at the margins. Some seasonal variation in the intensity of the lip markings has been observed.

*Gynandrium.*—Color — color fan 1, yellow group 13(A).

*Pollen cap.*—Color — color fan 4, white group 157(B).

Fragrance: Present but reduced from that of the Cymbidium Golden Elf 'Sundust' female parent.

*Penduncle.*—Strong and erect without any arching. Length about 30" with a diameter of ⅞". Membranous sheaths persistent but brown at the point of flower opening. Mid-green with a high level of anthrocyanin pigmentation.

*Hardiness of plant.*—The new variety has flourished in night temperatures at Belle Glade, Fla. between 43 degrees F. in January and 70 degrees F. average in August, with daytime temperatures as high as 95 degrees F.

*Disease resistance.*—No observations have been made except that root growth is encouraged in a rockwool medium and slightly retarded in spaghnum moss.

*Seed development.*—Seed development has not been observed and the predicted ploidy would suggest a high level of sterility. Attempted crossings in 1998, 1999, and 2000 have failed to produce viable embryo's when green pod cultured in vitro.

I claim:

1. It is claimed that this is a new and distinct variety of pot plant Cymbidium named 'Everglades Gold' as illustrated and described.

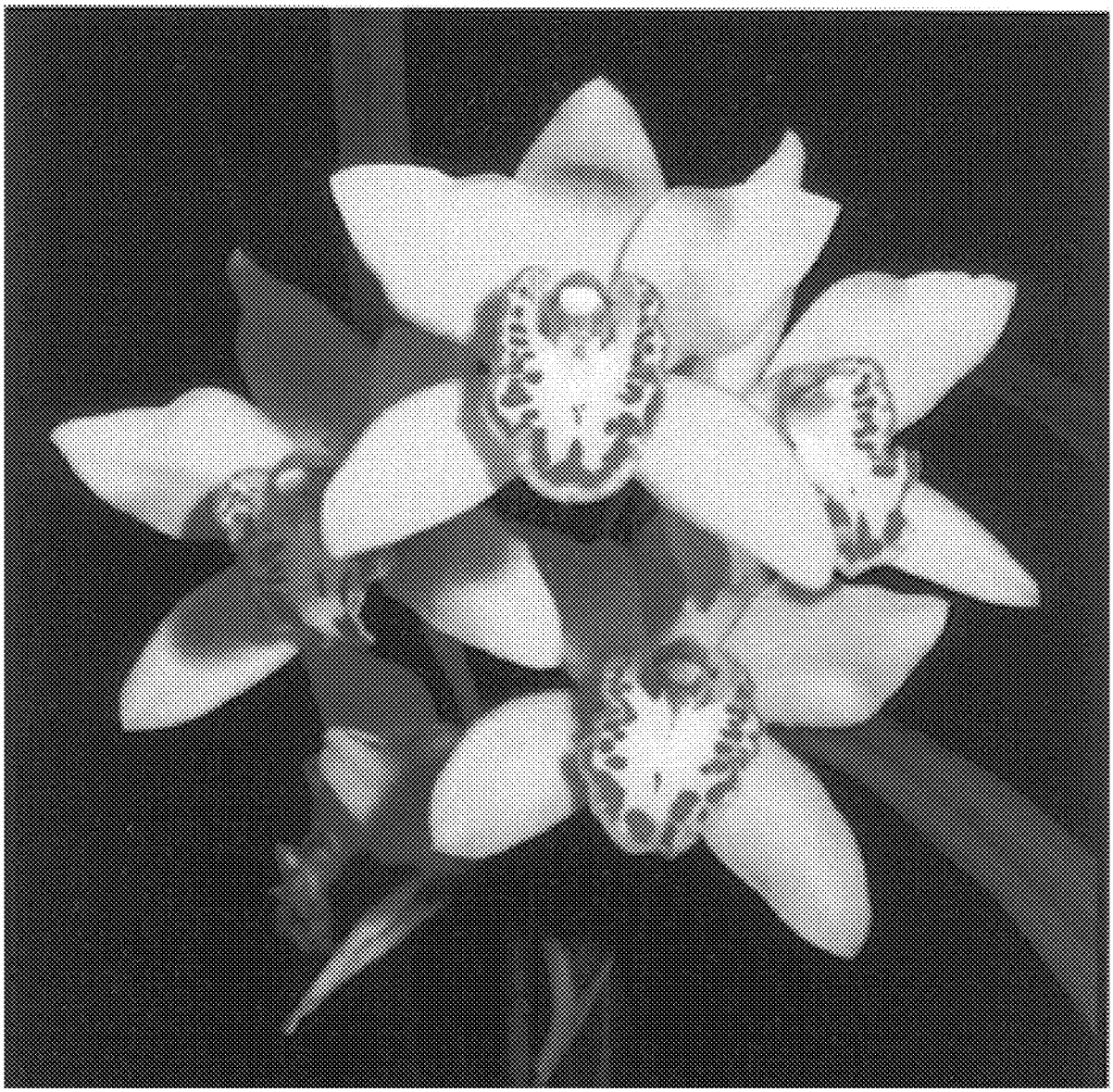

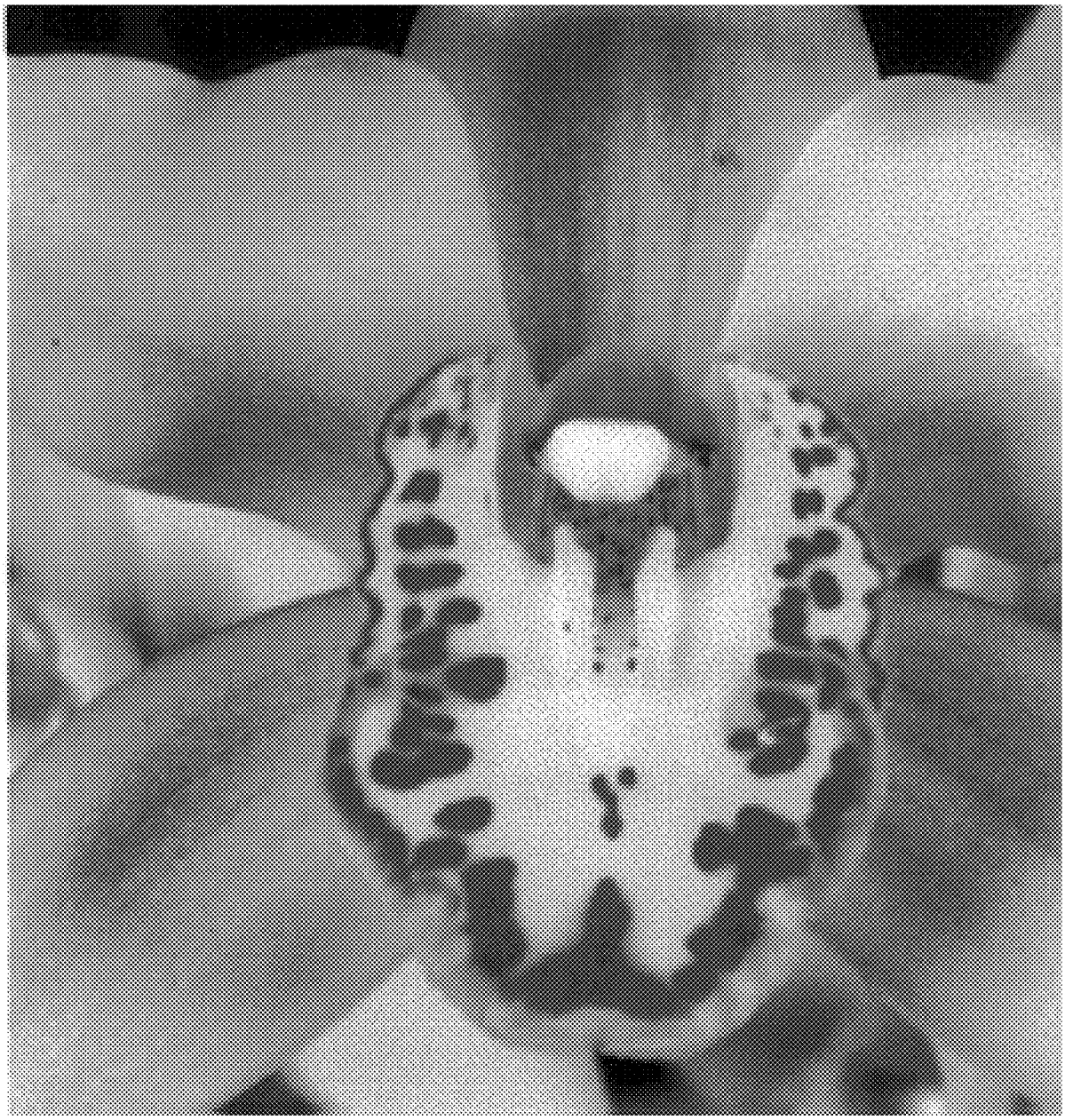

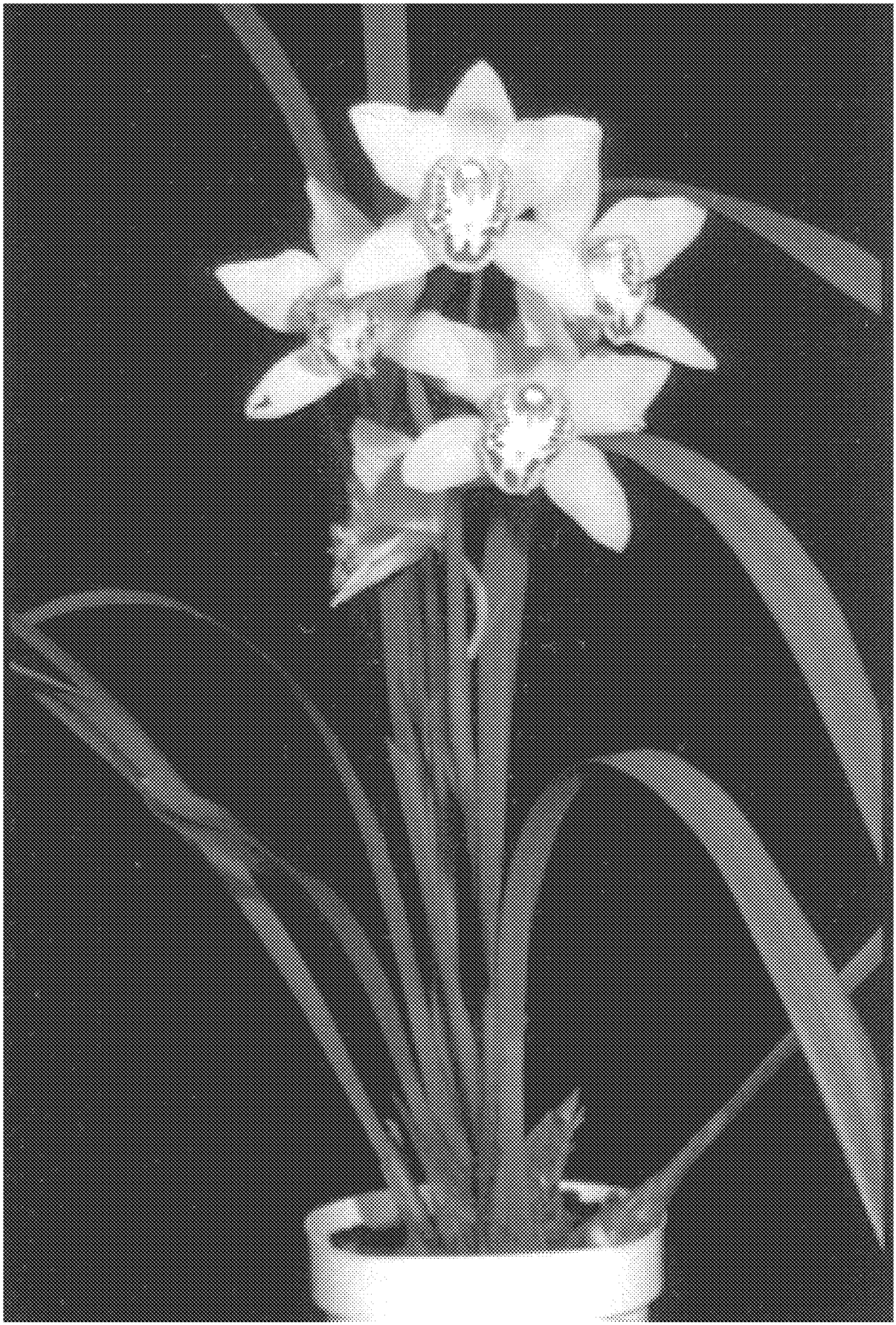

* * * * *